United States Patent
Sako et al.

(10) Patent No.: US 8,966,385 B2
(45) Date of Patent: Feb. 24, 2015

(54) RADIATION IMAGING APPARATUS, DISPLAY PROCESSING METHOD OF THE SAME, AND COMPUTER-READABLE STORAGE MEDIUM

(75) Inventors: Tsukasa Sako, Yokohama (JP); Koji Takekoshi, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 630 days.

(21) Appl. No.: 12/763,835

(22) Filed: Apr. 20, 2010

(65) Prior Publication Data
US 2010/0299622 A1    Nov. 25, 2010

(30) Foreign Application Priority Data

May 20, 2009   (JP) ................................ 2009-122565

(51) Int. Cl.
| | | |
|---|---|---|
| G06F 3/048 | (2013.01) | |
| G06F 3/00 | (2006.01) | |
| G06F 19/00 | (2011.01) | |
| G06Q 50/24 | (2012.01) | |
| G06Q 50/22 | (2012.01) | |
| G06F 3/0481 | (2013.01) | |

(52) U.S. Cl.
CPC ............ *G06F 19/3406* (2013.01); *G06F 3/048* (2013.01); *G06Q 50/24* (2013.01); *G06Q 50/22* (2013.01); *G06F 3/0481* (2013.01); *G06F 19/321* (2013.01)
USPC ............... 715/764; 715/709; 715/861; 705/2; 705/3; 705/301; 705/924

(58) Field of Classification Search
CPC ..... G06Q 50/22; G06Q 50/24; G06Q 10/107; G06F 3/048; G06F 3/0481; G06F 19/322; G06F 19/36

USPC ........... 715/764, 709, 861; 705/2, 3, 301, 924
See application file for complete search history.

(56) References Cited

U.S. PATENT DOCUMENTS

| | | | | |
|---|---|---|---|---|
| 5,355,892 | A | * | 10/1994 | Saltzstein et al. ............. 600/523 |
| 5,827,071 | A | * | 10/1998 | Sorensen et al. .............. 434/323 |
| 6,137,860 | A | * | 10/2000 | Ellegood et al. ................ 378/58 |
| 6,307,561 | B1 | * | 10/2001 | Doi et al. ....................... 345/473 |
| 6,314,411 | B1 | * | 11/2001 | Armstrong ...................... 706/11 |
| 6,369,835 | B1 | * | 4/2002 | Lin ................................. 715/726 |
| 6,401,085 | B1 | * | 6/2002 | Gershman et al. .................... 1/1 |
| 6,574,629 | B1 | * | 6/2003 | Cooke, Jr. et al. .................... 1/1 |

(Continued)

FOREIGN PATENT DOCUMENTS

| | | |
|---|---|---|
| JP | 2003-265455 | 9/2003 |
| JP | 2010268923 A | * 12/2010 |

*Primary Examiner* — Ece Hur
(74) *Attorney, Agent, or Firm* — Cowan, Liebowitz & Latman, P.C (57) ABSTRACT

A radiation imaging apparatus for imaging a radiation image inputs an operation instruction from a user and performs display control of a screen that has an input region in which one or more information input regions for having various types of information input thereto are disposed, and a workflow region in which workflow information related to imaging of the radiation image is disposed. Here, when a confirmation instruction indicating confirmation of an operation is input, the radiation imaging apparatus moves the one or more information input regions of the input region toward a prescribed region of the workflow region, and performs display using animation that sequences the movement of the one or more information input regions.

9 Claims, 13 Drawing Sheets

(56) References Cited

U.S. PATENT DOCUMENTS

| | | | | |
|---|---|---|---|---|
| 6,603,494 B1* | 8/2003 | Banks et al. | | 715/807 |
| 6,795,572 B1* | 9/2004 | Matsuno | | 382/132 |
| 7,092,970 B2* | 8/2006 | Shiibashi et al. | | 1/1 |
| 7,371,177 B2* | 5/2008 | Ellis et al. | | 463/42 |
| 7,397,851 B2* | 7/2008 | Roman | | 375/240.01 |
| 7,609,259 B2* | 10/2009 | McBagonluri et al. | | 345/419 |
| 7,630,791 B2* | 12/2009 | Nguyen et al. | | 700/242 |
| 7,707,514 B2* | 4/2010 | Forstall et al. | | 715/810 |
| 7,752,556 B2* | 7/2010 | Forstall et al. | | 715/761 |
| 7,818,183 B2* | 10/2010 | Schoenberg | | 705/2 |
| 8,063,878 B2* | 11/2011 | Jung et al. | | 345/107 |
| 8,180,244 B2* | 5/2012 | Takubo et al. | | 399/81 |
| 8,214,758 B2* | 7/2012 | Tanaka | | 715/777 |
| 8,316,299 B2* | 11/2012 | Asaka et al. | | 715/716 |
| 2002/0165912 A1* | 11/2002 | Wenocur et al. | | 709/203 |
| 2003/0179245 A1* | 9/2003 | Akagi | | 345/804 |
| 2004/0240624 A1* | 12/2004 | Shiibashi et al. | | 378/197 |
| 2006/0097984 A1* | 5/2006 | Kim | | 345/156 |
| 2006/0117067 A1* | 6/2006 | Wright et al. | | 707/104.1 |
| 2006/0129933 A1* | 6/2006 | Land et al. | | 715/723 |
| 2006/0195521 A1* | 8/2006 | New et al. | | 709/204 |
| 2007/0078735 A1* | 4/2007 | Wan et al. | | 705/28 |
| 2007/0085840 A1* | 4/2007 | Asaka et al. | | 345/173 |
| 2008/0046293 A1* | 2/2008 | Yamada et al. | | 705/3 |
| 2008/0055252 A1* | 3/2008 | Miyake et al. | | 345/168 |
| 2008/0134082 A1* | 6/2008 | Delacroix et al. | | 715/790 |
| 2009/0142737 A1* | 6/2009 | Breig | | 434/178 |
| 2010/0042003 A1* | 2/2010 | Shiibashi | | 600/476 |
| 2010/0146422 A1* | 6/2010 | Seong et al. | | 715/765 |
| 2010/0235769 A1* | 9/2010 | Young et al. | | 715/764 |
| 2010/0321170 A1* | 12/2010 | Cooper et al. | | 340/425.5 |
| 2012/0092346 A1* | 4/2012 | Ording et al. | | 345/473 |
| 2012/0110052 A1* | 5/2012 | Smarr et al. | | 709/201 |

* cited by examiner

| EXAM | PAST |
|---|---|
| Work List | Manual | System |

PATENT LIST SEARCH ............ 81

NAME: [    ]  ACC#: [    ]
ID: [    ]  Study Date: [    ]

Narrowing: ○ All Exam  ○ New Exam  ○ Pending Exam  [    ] hour(s)ago

PATIENT LIST

| SEARCH RESULT | DATE | PATIENT ID | NAME | ... |
|---|---|---|---|---|
| | 2008/11/17 | 12345 | TARO PATENT | |
| | 2008/11/17 | 123 | HANAKO | |
| | 2008/11/14 | 5425 | adf | |
| | 2008/11/10 | 5983 | dafasdg | |
| | ... | | | |

On Line

[ < ] [ > ]  Delete

START

RADIATION IMAGING APPARATUS, DISPLAY PROCESSING METHOD OF THE SAME, AND COMPUTER-READABLE STORAGE MEDIUM

BACKGROUND OF THE INVENTION

1. Field of the Invention

The present invention relates to a radiation imaging apparatus, a display processing method of the same, and a computer-readable storage medium.

2. Description of the Related Art

X-ray imaging apparatuses using solid-state image sensors or the like have been developed, and now even with X-ray images, X-ray digital imaging technology using computers is becoming widespread.

With an apparatus equipped with X-ray digital imaging technology, a user inputs a patient's name on a computer and decides the imaging conditions under which imaging will be performed, and an X-ray image is displayed when imaging is subsequently performed.

When performing imaging, screens for inputting patient information (for example, reception list screen, search screen), screens for selecting imaging conditions and screens for displaying imaged images are used. With a conventional imaging apparatus, transition between these screens is realized in accordance with a predetermined workflow. Specifically, a transition switch for instructing transition to a screen to which transition is permitted is provided, and the user performs operations to transit between screens in a predetermined order. In this case, it is possible to allow the user to be aware of a workflow involving patient selection, examination start, imaging, and examination end (Japanese Patent Laid-Open No. 2003-265455).

However, with a conventional imaging apparatus, since transition could only be performed to a display screen to which transition was permitted, it was difficult for the user to comprehend what the operations he or she was performing at any given time were doing. Also, in the case where the imaging apparatus was configured so as to enable information to be input in various regions, it was difficult for the user to comprehend which settings were doing what.

SUMMARY OF THE INVENTION

The present invention provides a technique that improves operability by allowing the user to recognize setting items on various setting screens when performing radiation imaging.

According to a first aspect of the present invention there is provided a radiation imaging apparatus for imaging a radiation image, comprising: an input unit configured to input an operation instruction from a user; and a display control unit configured to perform display control of a screen that has an input region in which one or more information input regions for having various types of information input thereto are disposed, and a workflow region in which workflow information related to imaging of the radiation image is disposed, wherein the display control unit, when a confirmation instruction indicating confirmation of an operation is input by the input unit, moves the one or more information input regions of the input region toward a prescribed region of the workflow region, and performs display using animation that sequences the movement of the one or more information input regions.

According to a second aspect of the present invention there is provided a radiation imaging apparatus for capturing a radiation image, comprising: an input unit configured to input an operation instruction from a user; and a display control unit configured to perform display control of a screen that has an input region in which one or more information input regions for having various types of information input thereto are disposed, and a workflow region in which workflow information related to imaging of the radiation image is disposed, wherein the display control unit, when a confirmation instruction indicating confirmation of an operation is input by the input unit, moves the one or more information input regions of the input region toward a prescribed region of the workflow region from a boundary of the workflow region, while performing display.

Further features of the present invention will be apparent from the following description of exemplary embodiments with reference to the attached drawings.

DESCRIPTION OF THE EMBODIMENTS

Exemplary embodiments of the present invention will now be described in detail with reference to the drawings. It should be noted that the relative arrangement of the components, and the numerical expressions and numerical values set forth in these embodiments do not limit the scope of the present invention unless it is specifically stated otherwise.

It should be noted that while the following embodiments will be described using the case where X-rays are applied as radiation as an example, radiation is not limited to X-rays and may be electromagnetic waves, alpha rays, beta rays, gamma rays or the like.

Figure 1:
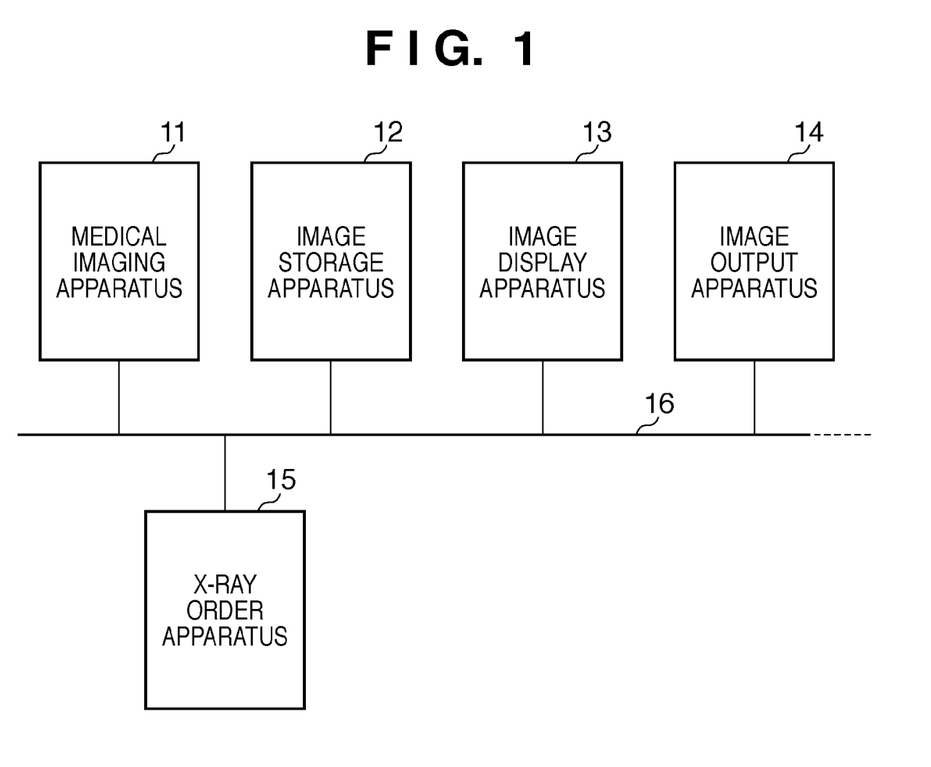
FIG. 1 shows an example of the overall configuration of a radiation imaging system.

FIG. 1 shows an example of the overall configuration of a radiation imaging system. It should be noted that the present embodiment will be described using the case where the radiation imaging apparatus according to an embodiment of the present invention is applied to a medical imaging apparatus as an example.

In the radiation imaging system, a medical imaging apparatus 11, an image storage apparatus 12, an image display apparatus 13, an image output apparatus 14 and an X-ray order apparatus 15 are connected via a network 16 constituted by a LAN (Local Area Network) or the like. It should be noted that the various apparatuses need only be able to communicate, and do not necessarily have to be connected via the network 16. For example, the apparatuses may be connected via a USB (Universal Serial Bus) or IEEE 1394, or via a WAN (Wide Area Network).

The medical imaging apparatus 11 performs X-ray imaging. The medical imaging apparatus 11 is typified by an X-ray CT or MRI apparatus, and is also called a modality, for example. The image storage apparatus 12 stores images imaged by the medical imaging apparatus 11, and is called a PACS (Picture Archiving and Communication System), for example.

The image display apparatus 13 displays images. The user refers to images displayed on the image display apparatus 13, and carries out image diagnosis or the like. The image output apparatus 14 prints X-ray images to film, paper or the like. The X-ray order apparatus 15 issues imaging orders, and is called an RIS (Radiology Information System), for example.

While an example of the overall configuration of a radiation imaging system is described above, the apparatuses provided in this system do not necessarily have to be realized as depicted above. For example, in the case of film-less operation, the image output apparatus 14 may be omitted. Also, a display device may be provided in the medical imaging apparatus 11, for example.

Also, one or more computers are built into the abovementioned medical imaging apparatus 11, image storage apparatus 12, image display apparatus 13, image output apparatus 14 and X-ray order apparatus 15. The one or more computers may be equipped with a main control unit such as a CPU, and a storage unit such as a ROM (Read Only Memory), a RAM (Random Access Memory), or the like, for example. Also, the one or more computers may be equipped with a communication unit such as a network card, and an input/output unit such as a keyboard, a mouse, a display or a touch panel. It should be noted that the various constituent elements are connected via a bus or the like, and are controlled by the main control unit executing programs stored in a storage unit.

Figure 2:
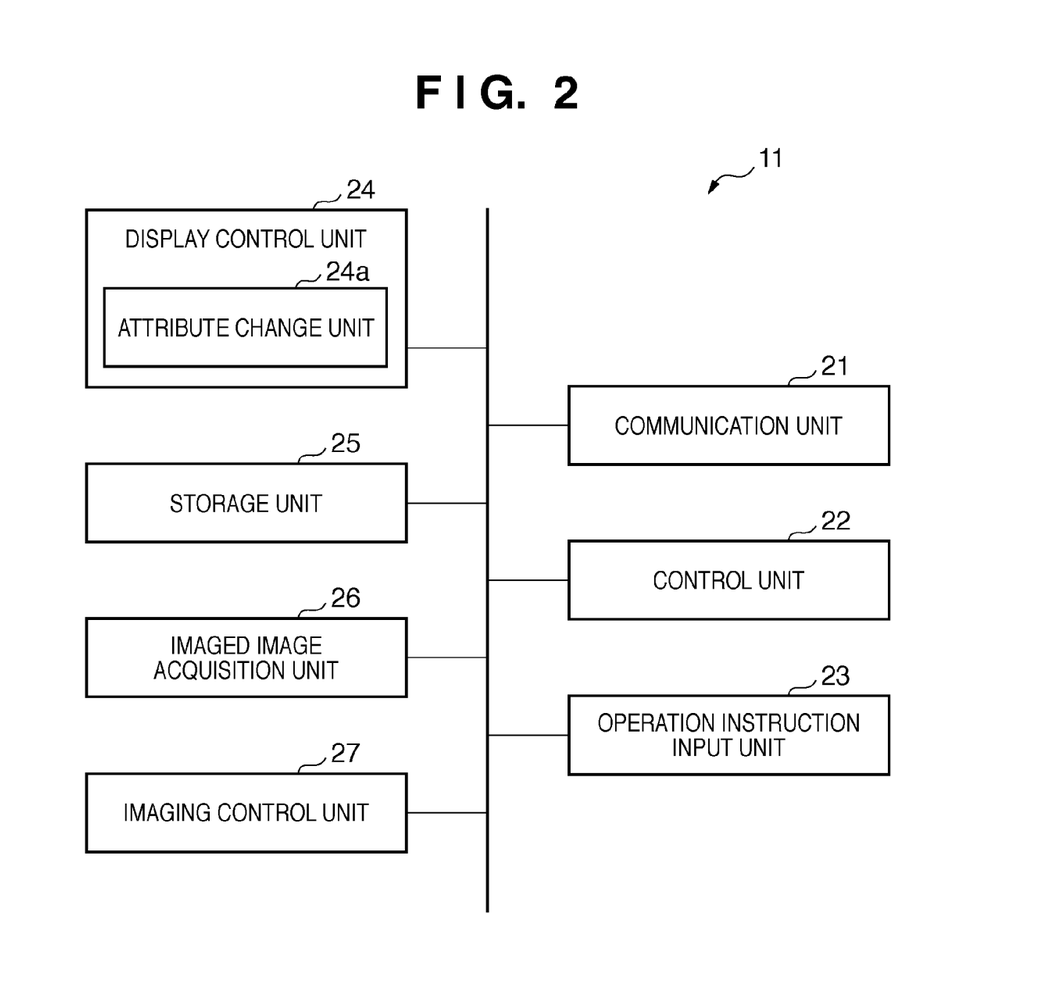
FIG. 2 shows an example of the functional configuration of a medical imaging apparatus 11 shown in FIG. 1.

Here, an example of the functional configuration of the medical imaging apparatus 11 shown in FIG. 1 will be described using FIG. 2.

The medical imaging apparatus 11 is constituted by being equipped with a communication unit 21, a control unit 22, an operation instruction input unit 23, a display control unit 24, a storage unit 25, an imaged image acquisition unit 26, and an imaging control unit 27.

The communication unit 21 functions as a communication interface that transmits and receives various types of information via the network 16. The control unit 22 performs overall control of operations in the medical imaging apparatus 11. The operation instruction input unit 23 inputs operation instructions from the user to the apparatus. It should be noted that operation instructions are input based on operation of a keyboard, a mouse or the like by the user.

The display control unit 24 controls display of various screens (GUIs). In the present embodiment, various screens are displayed on the image display apparatus 13 under display control of the display control unit 24. An attribute change unit 24a for changing attributes is provided in the display control unit 24. The attribute change unit 24a changes input-enabled text regions to a protected state (input-disabled regions), for example.

The storage unit 25 stores various types of information. Patient information, image information and the like is stored in the storage unit 25, for example. The imaged image acquisition unit 26 acquires imaged X-ray images. Specifically, the imaged image acquisition unit 26 acquires X-ray images imaged by an X-ray sensor. The imaging control unit 27 controls imaging of X-ray images. Imaging control is performed based on imaging conditions set by the user, for example.

Next, the various screens (GUIs) displayed on the image display apparatus 13 by the medical imaging apparatus 11 will be described using FIGS. 3 to 9.

Figure 3:
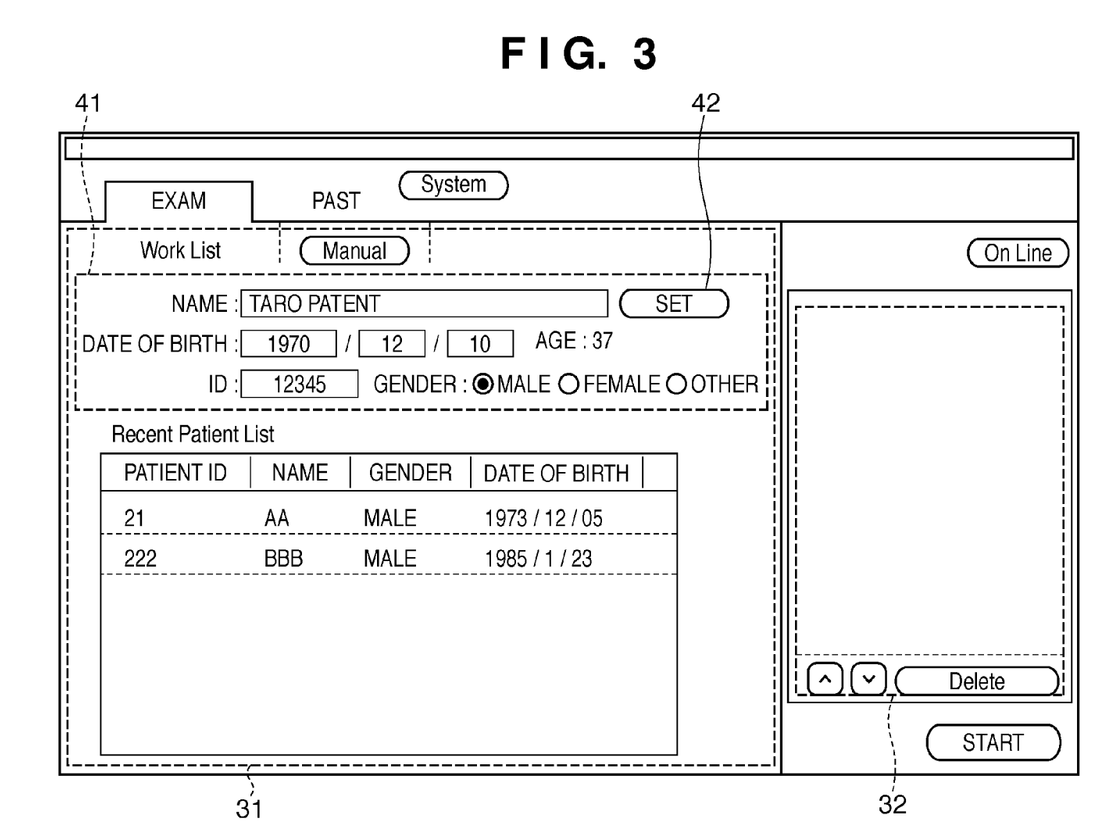
FIG. 3 shows an example of a screen configuration.

Here, firstly, the screens in the present embodiment are constituted to have an input region 31 and a workflow region 32, as shown in FIG. 3. The input region 31 is a region in which the display content is switched following screen transition, and is constituted to include one or more information input regions for having various types of information input thereto. In contrast, the progress situation (workflow information) is displayed in the workflow region 32 without being switched, even when the display content of the input region 31 transits between the start of imaging preparation and the end of imaging.

The user firstly inputs patient information when imaging is started. Here, a patient information input region 41 for having patient information input thereto is provided in the input region 31. The user uses a keyboard or the like to input patient information (patient name, date of birth, ID, gender, etc.) in text fields or radio buttons in this region. Once input is complete, the user presses a set button 42 for instructing confirmation of input information, using a mouse or the like. Following this, the input region 31 starts the screen transition shown in FIG. 4. Specifically, the patient information input region 41 changes in size while moving over a period of 1 second, for example, to a prescribed region in an upper portion of the workflow region 32 shown by 4B of FIG. 4. That is, following the confirmation instruction, the patient information input region 41 is scaled down and displayed in a patient information display region 43.

Figure 4:
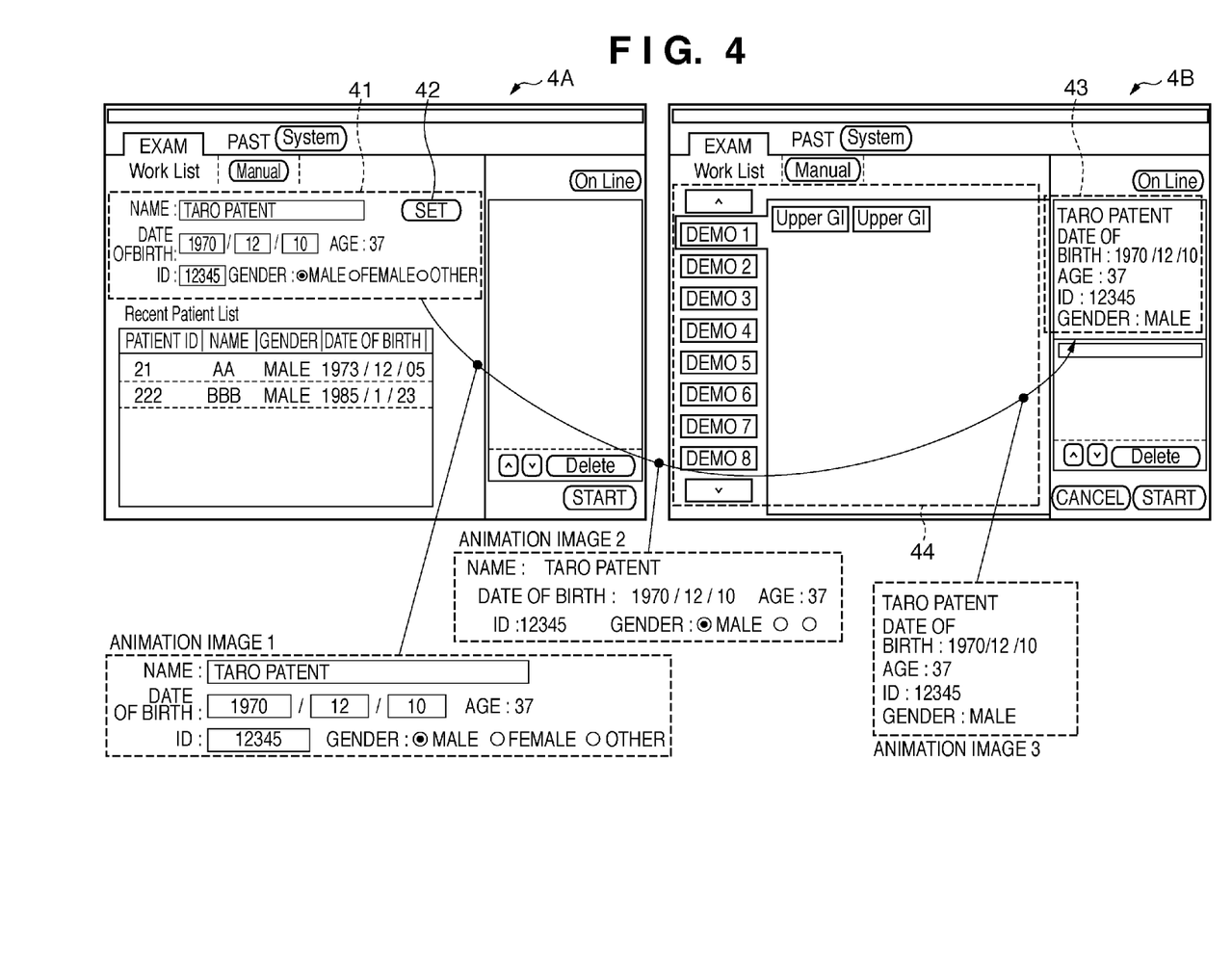
FIG. 4 shows an example of a change in the mode of display.

The patient information display region 43 of the workflow region 32 is in a protected state, with input being disabled. Specifically, the attributes of the patient name region, date of birth region, and ID region moved from the input region 31 are changed from input-enabled region to input-disabled region. Also, the gender region, in the input region 31, is constituted by radio buttons, but after being disposed in the patient information display region 43 is constituted only by text indicating gender.

Here, when moving the patient information input region 41, this region moves together with a sequence of animation, as shown by animation images 1 to 3. At this time, the radio buttons are gradually erased, and text indicating gender gradually appears, for example.

It should be noted that the mode of display is not limited thereto, and that there is also an alternative display mode (transparency mode). In transparency mode, the patient information display region 43 is moved and displayed in the upper portion of the workflow region 32 shown by 4B of FIG. 4, with the degree of transparency thereof gradually being reduced from the left boundary position of the workflow region 32, for example. That is, in this mode, the patient information display region 43 is displayed while moving slowly from being transparent to being clearly defined (see FIG. 9 discussed hereinafter).

At the same time that the movement of the patient information input region 41 is completed, a protocol selection region 44 moves from the left (top left in this case) to the right over a period of 1 second, for example, and is disposed in the input region 31. It should be noted that rather than waiting for the movement of the patient information input region 41 to be completed, the sliding of the protocol selection region 44 (to the right from left side) may be started after the start of the movement of the patient information input region 41, such as 0.5 seconds after, for example. It should be noted that the display timing can be appropriately changed by a UI setting. In the present embodiment as described above, display is performed using a sequence of animation. The user is thereby able to recognize which information is in what position more easily than the case where information is displayed instantaneously.

Here, once input of patient information has finished, the user performs protocol selection. That is, the user decides the imaging technique. Protocol selection is performed based on operations from a screen shown in FIG. 5A, for example. The protocol selection region 44 for performing protocol selection is disposed in the input region 31, and the user presses one of protocol buttons 52 which are located in this region to select a protocol.

Figure 5A:
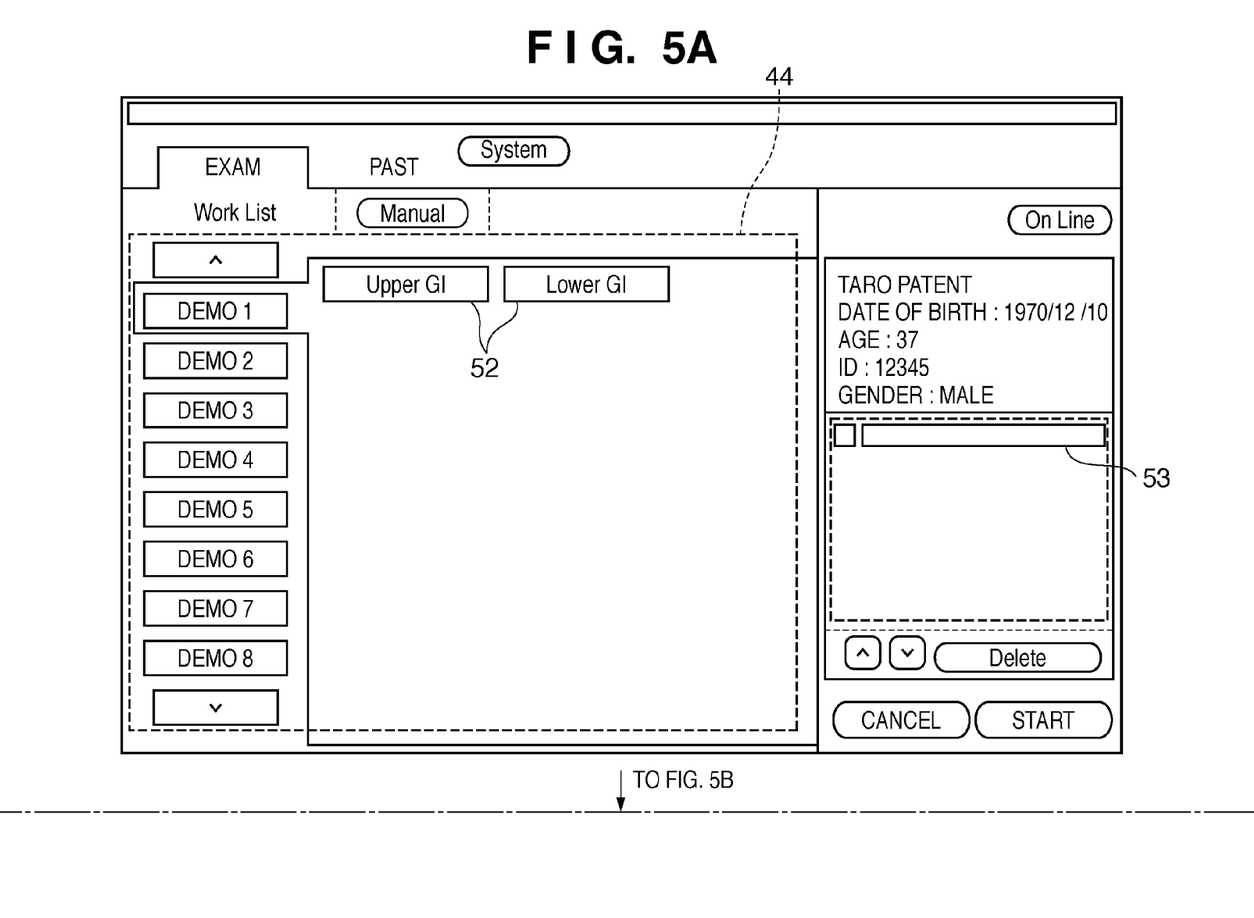
FIGS. 5A and 5B show an example of a change in the mode of display.
Figure 5B:
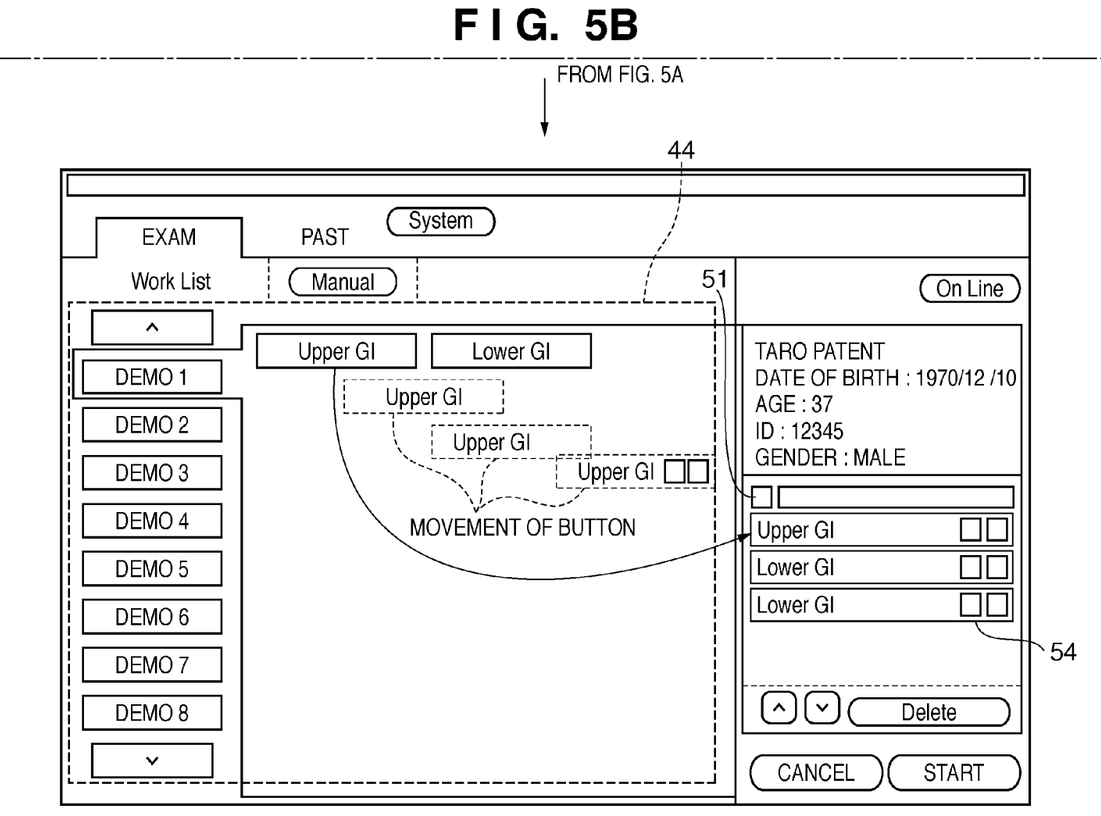

Following this button press, the pressed protocol button 52 moves to a protocol list region 53 of the workflow region 32 shown in FIG. 5B over a period of 1 second, for example, while at the same time changing in size. At this time, the protocol buttons 52 located at the origin of the move continue to be displayed. The user is thereby able to reselect the same protocol.

Figure 6:
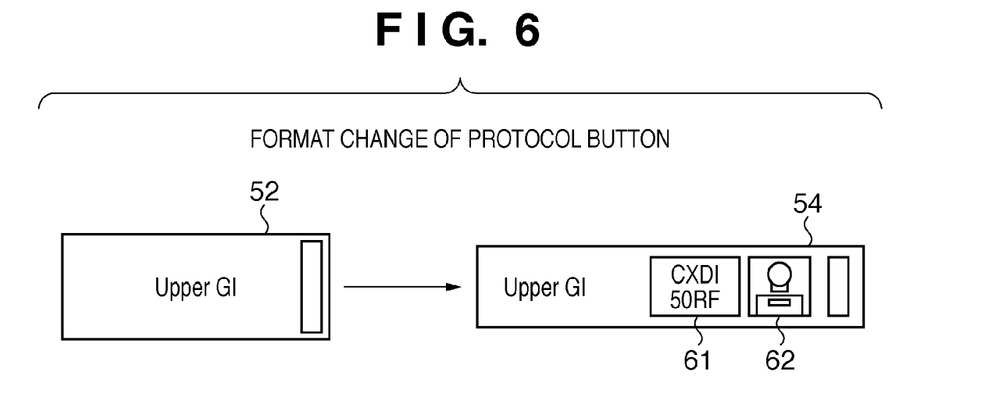
FIG. 6 shows an example of a change in the mode of display.

Here, when a protocol button 52 moves, the button size increases over a period of 1 second, for example, and also the format changes (attribute information is added), as shown in FIG. 6. Icons such as a sensor type 61 and a mount type 62 are gradually displayed and disposed in the space created by the increase in size. It should be noted that the protocol buttons 52 may be set to a protected state when changing the format, so as to disable pressing of the button.

It should be noted that the mode of display is not limited thereto, and that there is also an alternative display mode (transparency mode). In transparency mode, the protocol buttons 52 are moved and displayed in the protocol list region 53 when pressed, with the degree of transparency thereof gradually being reduced from the left boundary position of the workflow region 32. That is, in this mode, the protocol buttons 52 are displayed while moving slowly from being transparent to being clearly defined (see FIG. 9 discussed hereinafter).

The size of the protocol buttons 52 changes as the buttons move, and when finally disposed in the protocol list region 53, the buttons will be sorted such that identical sensor types are arranged sequentially, based on icon information (sensor type 61). Also, the user can reshuffle the disposal order of protocols based on desired attributes by pressing a sort button 51. For example, the disposal order of protocols can be reshuffled such that imaging at identical sites is sequential. In the case where the disposal order of protocols is thus changed, the imaging order changes, and imaging of the same site can, for example, be performed sequentially, enabling imaging to be performed in an order that conforms to the intent of the user.

Figure 7A:
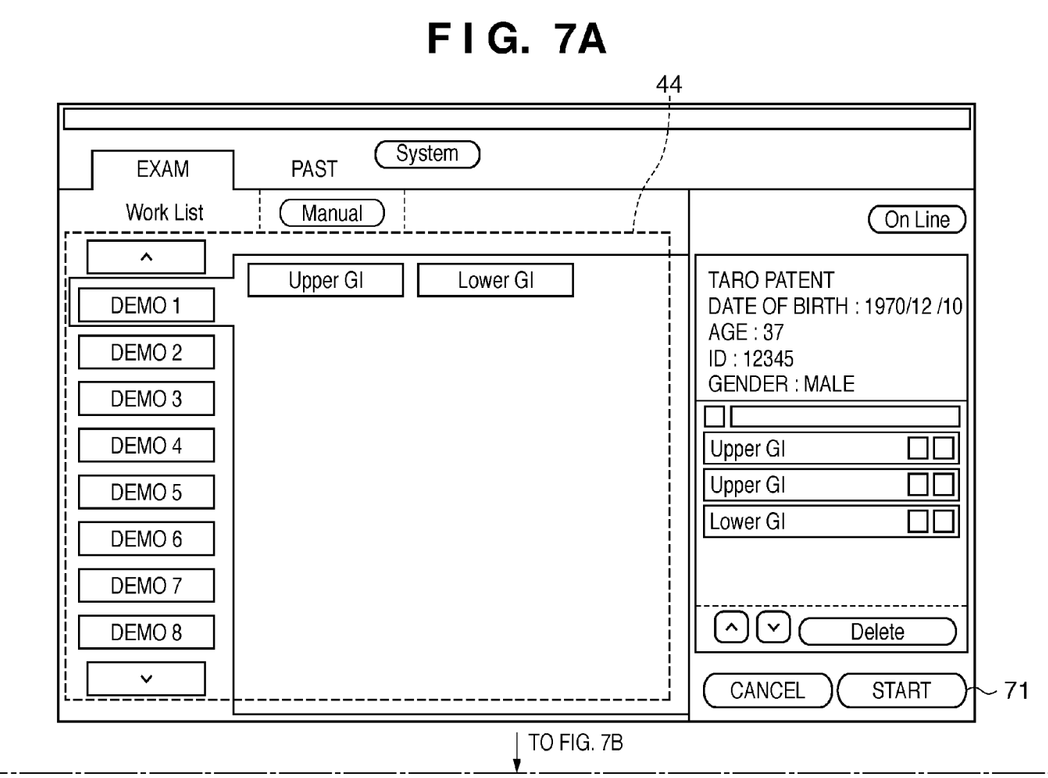
FIGS. 7A to 7C show an example of a change in the mode of display.
Figure 7B:
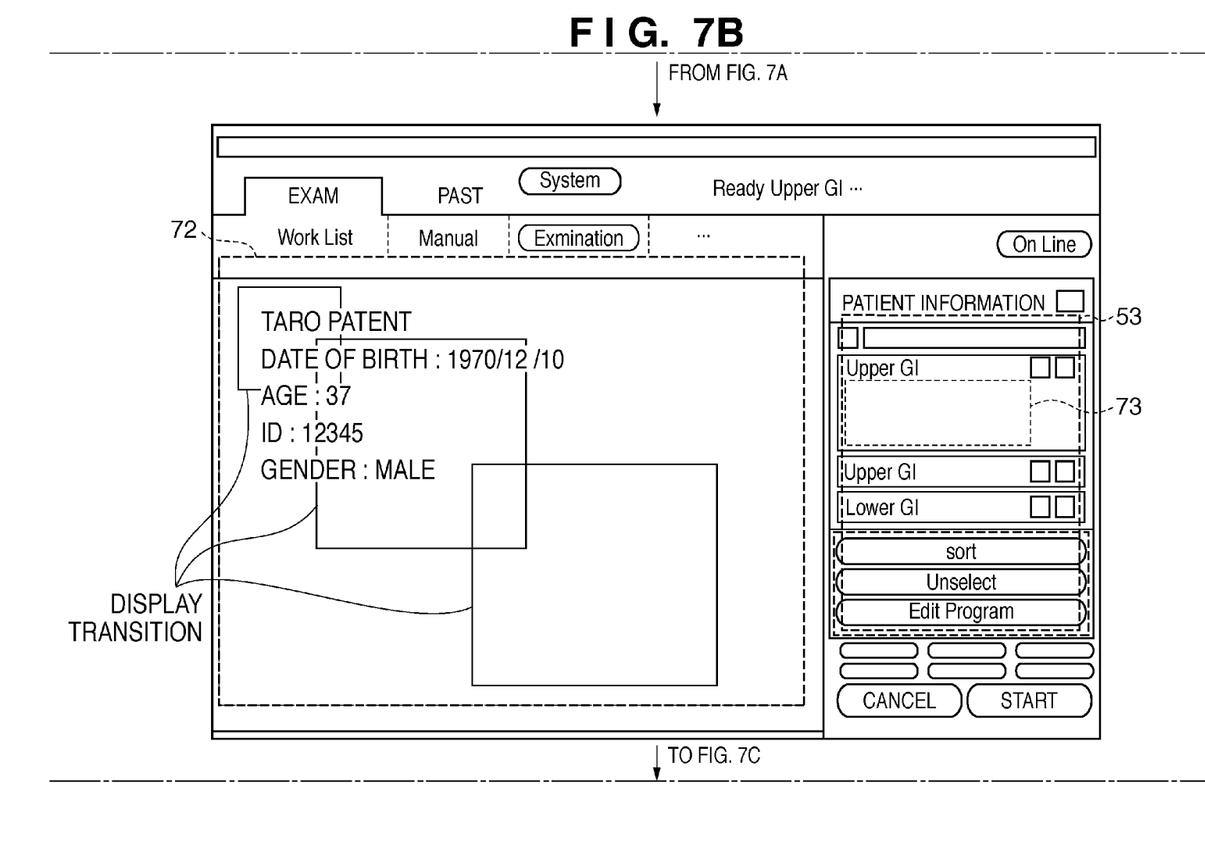

In order to perform X-ray imaging after one or more imaging techniques have thus been selected, the user instructs transition to an X-ray imaging screen using a keyboard, a mouse or the like. The protocol selection region 44 for selecting protocols is disposed in the input region 31 of the X-ray imaging screen, as shown in FIG. 7A. Here, when the user presses a start button 71, imaging of an X-ray image is started. Following this imaging, an X-ray imaging region 72 indicating the imaging range of an X-ray image moves over a period of 1 second, for example, from the left (top left in this case) toward the right (bottom right in this case), and is disposed in the protocol selection region 44, as shown in FIG. 7B. During or immediately after the transition of the X-ray imaging region 72, the mode of display changes so that one of protocol buttons 54 arrayed in the protocol list region 53 indicates imaging preparation. Specifically, the uppermost protocol in the protocol list region 53 becomes an active protocol 73, and an imaging preparation state and an X-ray imaging condition based on this protocol are set. Also, patient information is displayed in the X-ray imaging region 72 during or immediately after the transition of the X-ray imaging region 72, in a relatively large size compared with other information on the screen. The user is thereby able to accurately perceive patient information.

Figure 7C:
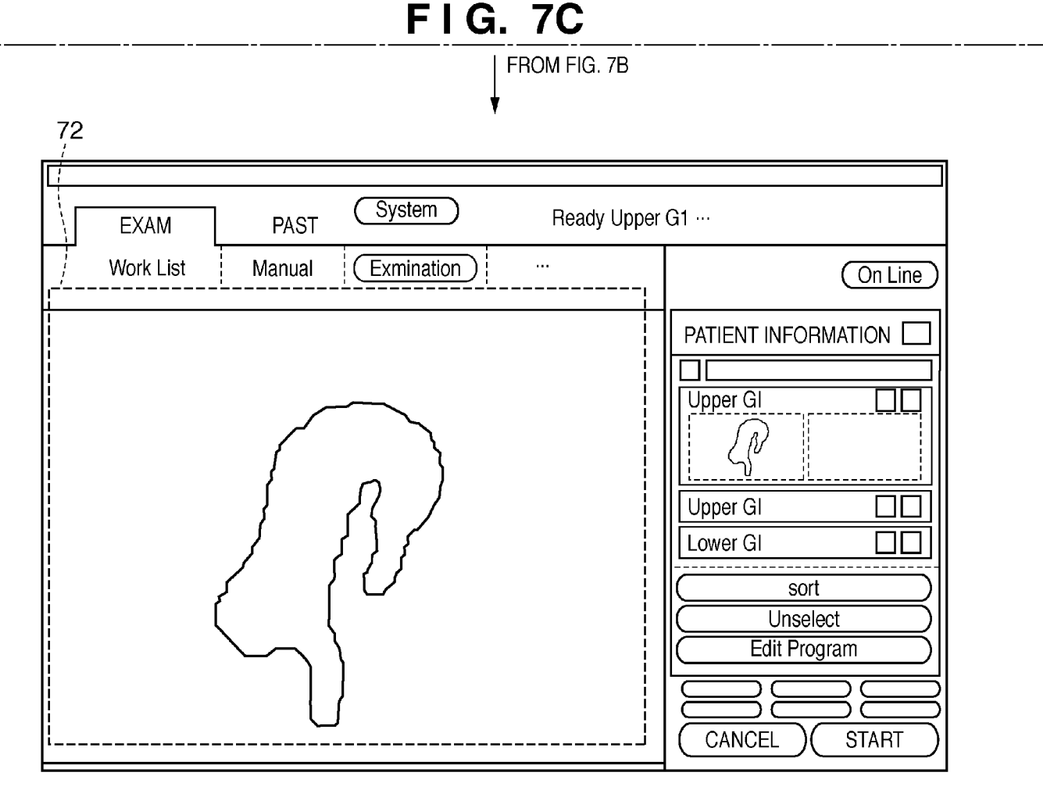

Subsequently, when imaging is performed, display of patient information disappears, and the imaged image is displayed in the X-ray imaging region 72, as shown in FIG. 7C. With the medical imaging apparatus 11, processing thus proceeds from input of patient information to protocol selection and X-ray imaging.

Next, the various screens (GUIs) when the medical imaging apparatus 11 and the X-ray order apparatus 15 shown in FIG. 1 are coordinated to perform imaging will be described (coordinated mode).

Figure 8A:
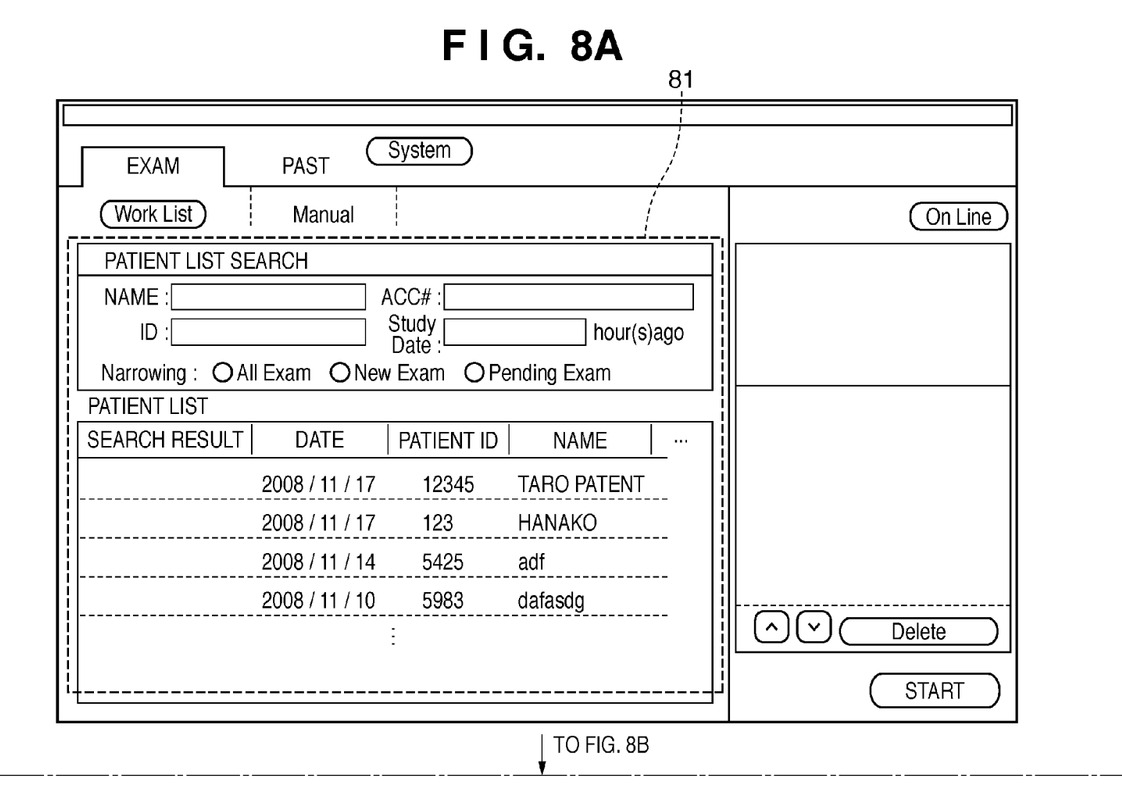
FIGS. 8A and 8B show an example of a change in the mode of display.

An examination order selection region 81 is disposed in the input region 31 of the screen shown in FIG. 8A, and a list of examination orders is displayed therein. The user selects one of the examination orders (includes patient name region, date of birth region, ID region, etc.) from this list using a mouse or the like. This selection operation serves as an input confirmation instruction, and following this instruction the selected examination order moves to a prescribed region in an upper portion of the workflow region 32 shown in FIG. 8B over a period of 1 second, for example, while at the same time changing in size. That is, following the confirmation instruction, the selected examination order is scaled down and displayed in the patient information display region 43.

Figure 8B:
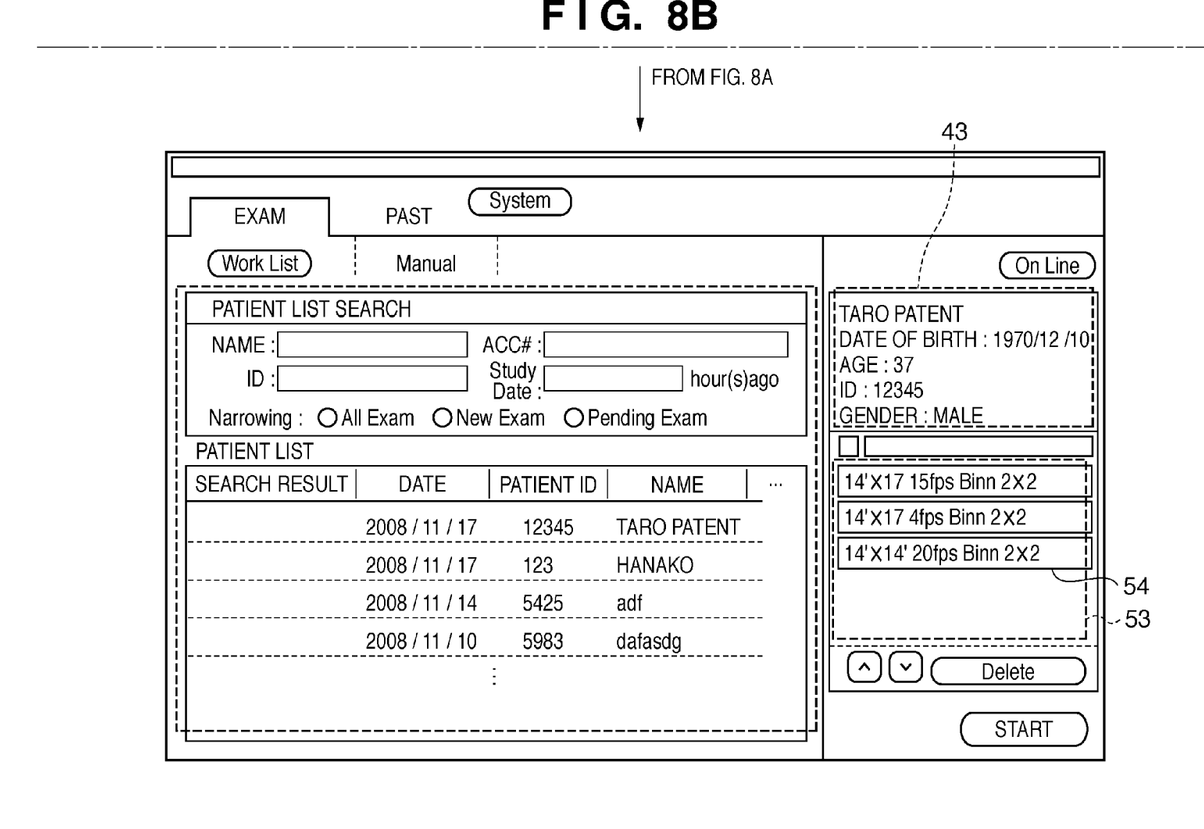

At this time, following movement of the examination order, the workflow region 32 is partitioned, and a protocol button 54 corresponding to the protocol ordered as an examination order is further generated. The generated protocol button 54 is disposed in the protocol list region 53.

Figure 9:
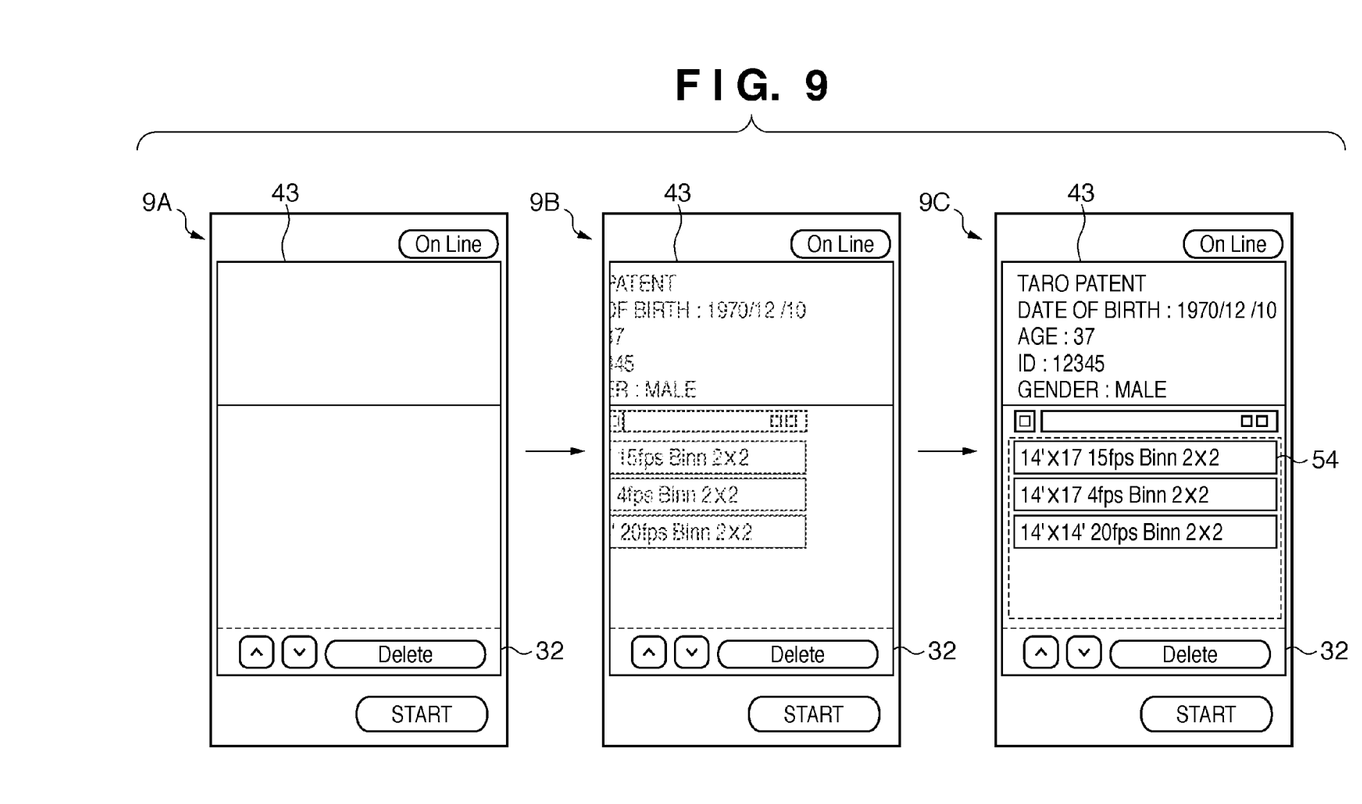
FIG. 9 shows an example of a change in the mode of display.

It should be noted that the mode of display is not limited thereto, and that there is also an alternative display mode (transparency mode). In transparency mode, the patient information display region 43 is moved and displayed in the upper portion of the workflow region 32, with the degree of transparency thereof gradually being reduced from the left boundary position of the workflow region 32, as shown in FIG. 9, for example. Further, at the same time as this movement of the patient information display region 43, the protocol buttons 54 corresponding to the protocols ordered as examination orders are displayed in the protocol list region 53. When performing this display, the protocol buttons 54 are moved and displayed, with the degree of transparency thereof gradually being reduced from the left boundary position of the workflow region 32. That is, in this mode, the patient information display region 43 and the protocol buttons 54 are displayed while moving slowly from being transparent to being clearly defined.

According to the present embodiment as described above, it is possible to allow the user to recognize setting items on the various screens when radiation imaging is performed. Thus, because display that is intuitively easy to understand can be provided to the user, operability can be improved. The user is thereby able to easily grasp what needs to be input to which region, even in the case where the GUI region is large, and information input is required in different regions in this large region.

Preferred embodiments of the present invention were described above, although the present invention is, needless to say, not intended to be limited to these embodiments, and may be modified or changed within the scope of the gist thereof.

For example, description was given above using the case where the abovementioned processing is implemented in the medical imaging apparatus 11 as an example, but this processing may, of course, be applied to and implemented by another apparatus, such as an ophthalmic imaging apparatus.

The present invention enables operability to be improved, since it is possible to allow the user to recognize setting items on various setting screens when radiation imaging is performed.

Other Embodiments

Aspects of the present invention can also be realized by a computer of a system or apparatus (or devices such as a CPU or MPU) that reads out and executes a program recorded on a memory apparatus to perform the functions of the above-described embodiments, and by a method, the steps of which are performed by a computer of a system or apparatus by, for example, reading out and executing a program recorded on a memory apparatus to perform the functions of the above-described embodiments. For this purpose, the program is provided to the computer for example via a network or from a recording medium of various types serving as the memory apparatus (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-122565, filed on May 20, 2009, which is hereby incorporated by reference herein in its entirety.

What is claimed is:

1. A radiation imaging apparatus for imaging a radiation image, comprising:
   a display control unit configured to display protocol buttons in an information input region for inputting information for radiation imaging, and a workflow region in which workflow information related to imaging of the radiation image is disposed, and
   a selection unit configured to select one of the protocol buttons in the information input region,
   wherein the display control unit displays movement of the selected protocol button in the information input region toward the workflow region using animation for changing a format of the selected protocol button if the protocol button is selected, and
   wherein the protocol button moved from the information input region to the workflow region is sorted such that the protocol buttons corresponding to types of sensors for imaging radiation images are arranged, and
   wherein the display control unit includes an attribute change unit configured to change the selected protocol button to an input-disabled button, when changing the format of the selected protocol button.

2. The radiation imaging apparatus according to claim 1, wherein the display control unit changes a format of one or more information input regions while performing display, when moving the one or more information input regions using the animation, and
   wherein the display control unit includes an attribute change unit configured to change the one or more information input regions to an input-disabled region, when changing the format of the one or more information input regions.

3. The radiation imaging apparatus according to claim 1, wherein the display control unit changes a format of one or more information input regions while performing display, when moving the one or more information input regions using the animation, and
   wherein the one or more information input regions are one or more patient information input regions for having patient information input thereto,
   the prescribed region of the workflow region is a patient information display region for having patient information based on the one or more patient information input region displayed therein, and
   the display control unit, during movement of the one or more patient information input regions or after movement of the one or more patient information input regions has ended, displays, in the input region, a protocol selection region for selecting an imaging technique for imaging the radiation image.

4. The radiation imaging apparatus according to claim 1, wherein the display control unit changes a format of one or more information input regions while performing display, when moving the one or more information input regions using the animation, and
   wherein the one or more information input regions are one or more buttons for selecting a protocol,
   the prescribed region of the workflow region is a protocol list region for having a list of protocols selected using the one or more buttons displayed therein, and
   the display control unit, during movement of the one or more buttons or after movement of the one or more buttons has ended, displays a display region for having the radiation image displayed therein.

5. The radiation imaging apparatus according to claim 4, wherein the display control unit displays, in the display region for having the radiation image displayed therein, information related to imaging, in a relatively large size compared with other information on the screen, and clears the display when the imaging ends.

6. The radiation imaging apparatus according to claim 4, wherein in the protocol list region, the selected protocols are arrayed in a prescribed direction in order of imaging, and
   the display control unit displays, in the protocol list region, a sort button for instructing a change in the order of the array based on an attribute of the protocols.

7. A display processing method of a radiation imaging apparatus for imaging a radiation image, comprising: displaying, by a display control unit, protocol buttons in an information input region for inputting information for radiation imaging, and a workflow region in which workflow information related to imaging of the radiation image is disposed, and selecting one of the protocol buttons in the information input region, wherein the display control unit displays movement of the selected protocol button in the information input region toward the workflow region using animation for changing a format of the selected protocol button if the protocol button is selected, and wherein the protocol button moved from the information input region to the work flow region is sorted such that the protocol buttons corresponding to types of sensors for imaging radiation images are arranged, wherein the display control unit includes an attribute change unit configured to change the selected protocol button to an input-disabled button, when changing the format of the selected protocol button.

8. A non-transitory computer-readable storage medium storing a computer program for causing a computer to function as: a display control unit configured to display protocol buttons in an information input region for inputting information for radiation imaging, and a workflow region in which workflow information related to imaging of the radiation image is disposed; and a selection unit configured to select one of the protocol buttons in the information input region, wherein the display control unit displays movement of the selected protocol button in the information input region toward the workflow region using animation for changing a format of the selected protocol button if the protocol button is selected, and wherein the protocol button moved from the information input region to the workflow region is sorted such that the protocol buttons corresponding to types of sensors for imaging radiation images are arranged, and wherein the display control unit includes an attribute change unit configured to change the selected protocol button to an input-disabled button, when changing the format of the selected protocol button.

9. A radiation imaging apparatus for imaging a radiation image, comprising:
   a display control unit configured to display protocol buttons in an information input region and a workflow region in which workflow information related to imaging of the radiation image is disposed; and
   a selection unit configured to select one of the protocol buttons in the information input region,
   wherein the display control unit displays movement of the selected protocol button in the information input region toward the workflow region using animation for transforming the shape of the information input region to the shape of the workflow region if the protocol button is selected, and
wherein the display control unit changes a format of the selected protocol button while performing display, when moving the selected protocol button using the animation,
wherein the protocol button moved from the information input region to the workflow region is sorted such that the protocol buttons corresponding to types of sensors for imaging radiation images are arranged,
wherein the display control unit includes an attribute change unit configured to change the selected protocol button to an input-disabled button, when changing the format of the selected protocol button.

* * * * *